US00PP29044P3

(12) United States Plant Patent
Hooijman

(10) Patent No.: US PP29,044 P3
(45) Date of Patent: Mar. 6, 2018

(54) ROSE PLANT NAMED 'ESM R202'

(50) Latin Name: *Rosa hybrida*
Varietal Denomination: ESM R202

(71) Applicant: ESMERALDA BREEDING B.V., Aalsmeer (NL)

(72) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 85 days.

(21) Appl. No.: 14/998,735

(22) Filed: Feb. 9, 2016

(65) Prior Publication Data

US 2017/0231129 P1 Aug. 10, 2017

(51) Int. Cl.
*A01H 5/02* (2006.01)

(52) U.S. Cl.
USPC ..... Plt./143

(58) Field of Classification Search
USPC ..... Plt./143
See application file for complete search history.

(56) References Cited

PUBLICATIONS

UPOV hit on Rose plant named 'ESM R202' QZ PBR 43825, published Oct. 15, 2014.*

* cited by examiner

*Primary Examiner* — Anne M Grunberg
(74) *Attorney, Agent, or Firm* — C. A. Whealy

(57) ABSTRACT

A new and distinct cultivar of Rose plant named 'ESM R202', characterized by its upright and strong flowering stems; vigorous growth habit and high productivity; dark green-colored leaves; yellow-colored flowers with light red-colored margins that are held on strong and long flowering stems within relatively large sprays; freely flowering habit with typically about eight flowers per spray and good productivity with about 13 to 14 flowering stems per plant produced per year; and excellent postproduction longevity.

1 Drawing Sheet

Botanical designation: *Rosa hybrida.*
Cultivar denomination: 'ESM R202'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'ESM R202'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in July, 2010 of a proprietary Rose selection identified as Line 95, not patented, as the female, or seed, parent with a proprietary Rose selection identified as Line 222, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in September, 2011.

Asexual reproduction of the new Rose plant by bud grafting in El Quinche, Pichincha, Ecuador since October, 2011 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R202'. These characteristics in combination distinguish 'ESM R202' as a new and distinct Rose plant:

1. Upright and strong flowering stems.
2. Vigorous growth habit and high productivity.
3. Dark green-colored leaves.
4. Yellow-colored flowers with light red-colored margins that are held on strong and long flowering stems within relatively large sprays.
5. Freely flowering habit with typically about eight flowers per spray and good productivity with about 13 to 14 flowering stems per plant produced per year.
6. Excellent postproduction longevity.

Plants of the new Rose differ from plants of the female parent selection in the following characteristics:

1. Plants of the new Rose have longer flowering stems than plants of the female parent selection.
2. Flowers of plants of the new Rose have more petals than flowers of plants of the female parent selection.
3. Plants of the new Rose and the female parent selection differ in flower color as plants of the female parent selection have pink-colored flower petals.

Plants of the new Rose differ from plants of the male parent selection in the following characteristics:

1. Plants of the new Rose are shorter than plants of the male parent selection.

2. Flower buds of plants of the new Rose are taller than flower buds of plants of the male parent selection.
3. Plants of the new Rose have more flowers per spray than plants of the male parent selection.
4. Flowers of plants of the new Rose have more petals than flowers of plants of the male parent selection.
5. Plants of the new Rose and the male parent selection differ in flower color as plants of the male parent selection have orange-colored flower petals.

Plants of the new Rose can be compared to plants of *Rosa hybrida* 'Double Vision', not patented. In side-by-side comparisons conducted in El Quinche, Pichincha, Ecuador, plants of the new Rose differed from plants of 'Double Vision' in the following characteristics:

1. Plants of the new Rose were taller than plants of 'Double Vision'.
2. Plants of the new Rose were more vigorous than plants of 'Double Vision'.
3. Plants of the new Rose were more freely branching and produced about twice as many flowering stems per year as plants of 'Double Vision'.
4. Flowers of plants of the new Rose had more petals than flowers of plants of 'Double Vision'.
5. Cut flowers of plants of the new Rose lasted about four days longer than cut flowers of plants of 'Double Vision'.
6. Plants of the new Rose and 'Double Vision' differed in flower color as plants of 'Double Vision' had white-colored petals with dark pink-colored margins.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the upper left of the sheet is a side perspective of a typical flowering stem of 'ESM R202' and the photograph at the bottom left of the sheet is a close-up view of a typical flowering stem of 'ESM R202'.

The photograph at the upper right of the sheet is a close-up view of a typical developed flower of 'ESM R202'.

The photographs at the lower right of the sheet are close-up views of the upper and lower surfaces of typical leaves of 'ESM R202'.

DETAILED BOTANICAL DESCRIPTION

The aforementioned photographs, following observations and measurements describe plants grown in 10-liter containers in a polyethylene-covered greenhouse in El Quinche, Pichincha, Ecuador and under typical hydroponic Rose production practices. Plants were pinched 13 to 14 weeks after planting and were 46 weeks old when the photographs were taken and 87 weeks old when the description was taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'ESM R202'.

Parentage:

*Female, or seed, parent.*—Proprietary seedling selection of *Rosa hybrida* identified Line 95, not patented.

*Male, or pollen, parent.*—Proprietary seedling selection of *Rosa hybrida* identified Line 222, not patented.

Propagation:

*Type.*—By bud grafting.

*Time to initiate roots, summer.*—About 15 days at temperatures about 26° C. to 30° C.

*Time to produce a rooted young plant, summer.*—About 30 days at temperatures about 22° C. to 26° C.

*Root description.*—Medium in thickness, fibrous; close to N199B and 200D in color.

*Rooting habit.*—Moderately freely branching; dense.

Plant description:

*Plant and growth habit.*—Perennial shrub; upright and strong flowering stems; typically grown as a spray-type cut flower; vigorous growth habit.

*Productivity.*—Plants of the new Rose are highly productive with about 13.56 flowering stems developing per plant per year.

*Plant height.*—About 129 cm.

*Plant width (spread).*—About 63 cm.

*Lateral branches.*—Quantity: Freely branching habit with about 18 lateral branches developing per plant. Length: About 141 cm. Diameter: About 7.3 mm. Internode length: About 4.8 cm. Texture: Smooth, glabrous; older stems, woody. Strength: Strong. Color: Close to 146A. Thorns: Density: Sparse. Shape: Triangular with sharp acuminate apices; slightly incurved. Height: About 9.8 mm. Length, at base: About 8.7 mm. Color, immature: Close to 178A and 199A. Color, mature: Close to 172A and 199A.

Leaf description:

*Arrangement.*—Alternate; compound with typically seven to nine leaflets per leaf.

*Leaf length.*—About 18 cm.

*Leaf width.*—About 11.4 cm.

*Terminal leaflet length.*—About 5.8 cm.

*Terminal leaflet width.*—About 3.8 cm.

*Lateral leaflet length.*—About 5.5 cm.

*Lateral leaflet width.*—About 3.7 cm.

*Leaflet shape.*—Ovate.

*Leaflet apex.*—Acute.

*Leaflet base.*—Short attenuate.

*Leaflet margin.*—Serrate.

*Leaflet texture, upper and lower surfaces.*—Smooth, glabrous; papery to coriaceous.

*Leaflet venation pattern.*—Pinnate.

*Leaflet color.*—Developing leaflets, upper surface: Close to 146B. Developing leaflets, lower surface: Close to 139A. Fully expanded leaflets, upper surface: Close to 139A; venation, close to 145A and 146A. Fully expanded leaflets, lower surface: Close to 147B; venation, close to 146C.

*Petioles, leaves.*—Length: About 1.5 cm. Diameter: About 1.9 mm. Texture, upper surface: Prickly. Texture, lower surface: Smooth, glabrous. Color, upper surface: Close to 146A and 152D. Color, lower surface: Close to 146D.

*Petioles, leaflets.*—Length: About 2.1 cm. Diameter: About 1.2 mm. Texture, upper surface: Prickly. Texture, lower surface: Smooth, glabrous. Color, upper surface: Close to 146A to 146D. Color, lower surface: Close to 146D.

*Stipules.*—Arrangement and appearance: Two, adnate to the petiole, leafy in appearance. Length: About 2.8 cm. Width: About 2.1 mm. Shape: Roughly deltoid. Apex: Acuminate, tapered. Base: Tapered. Margin: Entire. Texture, upper and lower surfaces: Pubescent; membranous. Venation pattern: Pinnate. Color, upper surface: Close to 137A. Color, lower surface: Close to 146A.

Flower description:

*Flower type and arrangement.*—Symmetrical rosette flowers; flowers typically grown as spray-types; flowers face upright; freely flowering with typically eight flowers per spray.

*Flowering season.*—Plants of the new Rose flower year-round under greenhouse conditions; early flowering habit, plants begin flowering about 79 days after pinching.

*Spray diameter.*—About 20 cm.

*Spray height.*—About 23 cm.

*Flower diameter.*—About 5.5 cm.

*Flower depth* (*height*).—About 3 cm.

*Flower longevity.*—Excellent postproduction longevity; flowers maintain good substance for about 34 to 36 days on the plant and for about 16 days as a cut flower; flowers persistent.

*Fragrance.*—Slightly fragrant.

*Flower buds.*—Rate of opening: About 20 to 22 days. Length: About 3.1 cm. Diameter: About 2.6 cm. Shape: Ovoid. Color: Close to 144A and 183A.

*Petals.*—Quantity: About 39 per flower; petals imbricate. Length: About 2.8 cm. Width: About 3.2 cm. Shape: Nearly round; transversely ovate. Apex: Short acute. Base: Obtuse. Margin: Entire. Texture, upper and lower surfaces: Smooth, glabrous; papery to coriaceous. Color: When opening, upper surface: Close to 3C; towards the base, close to 153D; towards the apical margin, close to 42A. When opening, lower surface: Close to 154D; towards the base, close to 153D; towards the apical margin, close to 26C. Fully opened, upper surface: Close to 1C; towards the base, close to 1A; towards the apical margin, close to 45C. Fully opened, lower surface: Close to 150D; towards the base, close to 160A; towards the apical margin, close to 52A.

*Petaloids.*—Quantity: About seven; whorled. Length: Variable. Width: Variable. Shape: Irregularly shaped. Apex: Blunt to short acute. Base: Obtuse. Margin: Mostly uneven. Texture, upper and lower surfaces: Smooth, glabrous; papery to coriaceous. Color: When opening, upper and lower surfaces: Close to N30A and 5A. Fully opened, upper and lower surfaces: Close to 154C and 41A.

*Sepals.*—Quantity per flower: Typically five in a single whorl. Length: About 3.3 cm. Width: About 1.3 cm. Shape: Roughly deltoid. Apex: Tapered. Base: Truncate. Margin: Entire; ciliate and/or glandular. Texture, upper and lower surfaces: Leathery. Color: When opening, upper surface: Close to 146C. When opening, lower surface: Close to 146B. Fully opened, upper surface: Close to 145A and 146B. Fully opened, lower surface: Close to 144A.

*Pedicels.*—Length: About 3.3 cm. Diameter: About 2.5 mm. Strength: Strong. Angle: About 32° from vertical. Texture: Glabrous. Color: Close to 144A and N199A.

*Reproductive organs.*—Stamens: Quantity: About 112 per flower. Anther length: About 2.2 mm. Anther shape: Reniform. Anther color: Close to N163C and 160A. Filament color: Close to 151D. Pollen amount: Abundant. Pollen color: Close to N163C. Pistils: Quantity: About 123 per flower. Pistil length: About 1.2 cm. Stigma shape: Broadly reniform. Stigma color: Close to 153D. Style length: About 8 mm. Style color: Close to 157A. Receptacle height: About 9.3 mm. Receptacle diameter: About 9.3 mm. Receptacle shape: Cup-shaped. Receptacle texture: Smooth, glabrous. Receptacle color: Close to 144A. Fruits and seeds: Fruit and seed development have not been observed on plants of the new Rose.

Pathogen & pest tolerance: Plants of the new Rose have been observed to have good tolerance to Powdery Mildew, Downy Mildew and *Botrytis*. Plants of the new Rose have not been observed to be tolerant to pests and other pathogens common to Rose plants.

Temperature tolerance: Plants of the new Rose have been observed to tolerate temperatures ranging from 0° C. to 35° C.

It is claimed:

1. A new and distinct Rose plant named 'ESM R202' as illustrated and described.

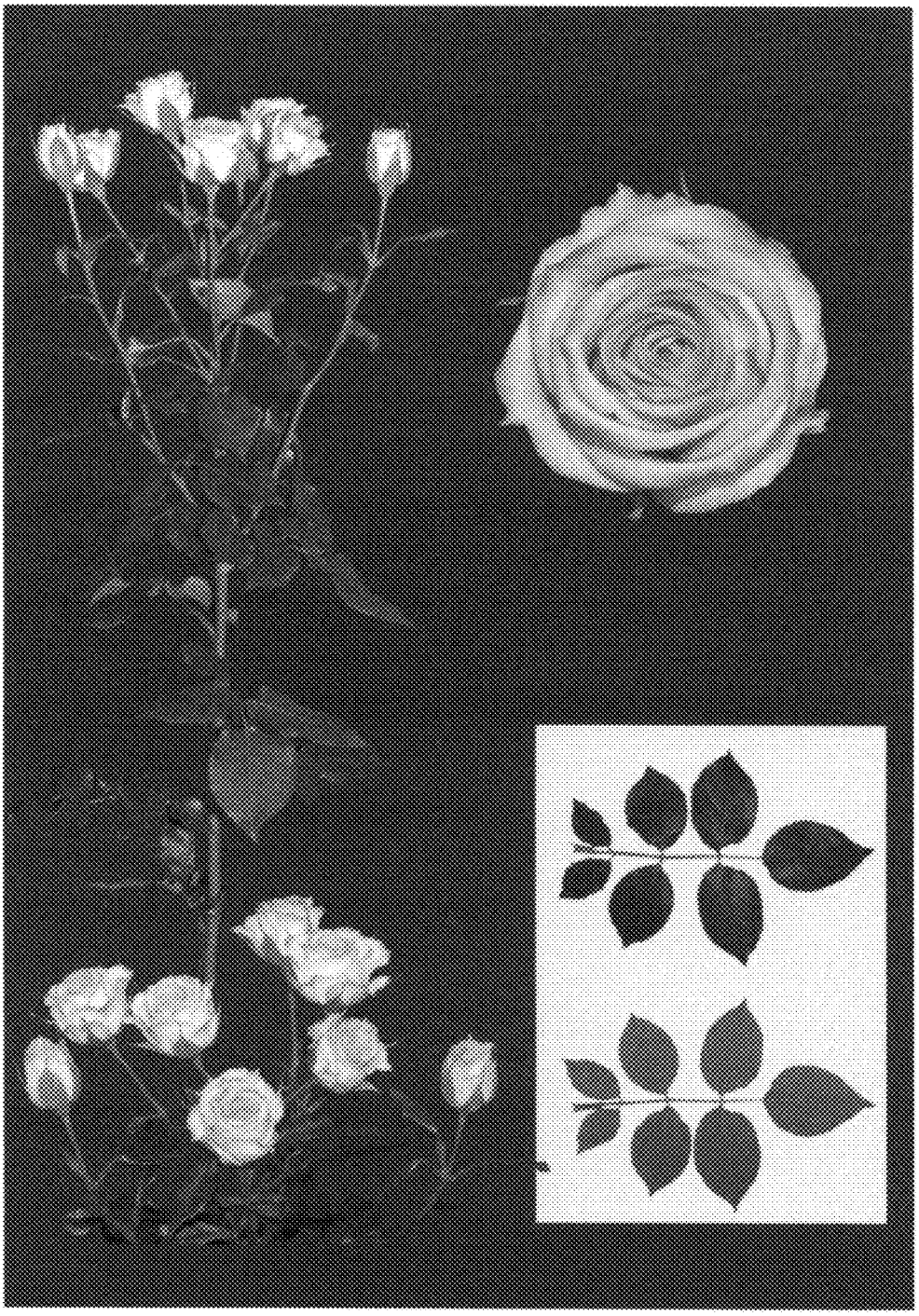

* * * * *